United States Patent [19]

Roth

[11] Patent Number: 5,629,342

[45] Date of Patent: *May 13, 1997

[54] ANTIMICROBIAL COMPOSITIONS

[75] Inventor: Willy Roth, Strengelbach, Switzerland

[73] Assignee: Akzo Nobel Chemicals Inc., Chicago, Ill.

[*] Notice: The term of this patent shall not extend beyond the expiration date of Pat. No. 5,488,065.

[21] Appl. No.: 591,326

[22] Filed: Jan. 25, 1996

Related U.S. Application Data

[63] Continuation of Ser. No. 859,189, Apr. 28, 1986, Pat. No. 5,488,065, which is a continuation of Ser. No. 670,246, Nov. 13, 1984, abandoned.

[30] Foreign Application Priority Data

Nov. 17, 1983 [CH] Switzerland .................... 6184/83

[51] Int. Cl.⁶ .................................................. A61K 31/285
[52] U.S. Cl. ................................................................. 514/504
[58] Field of Search ............................................... 514/504

[56] References Cited

U.S. PATENT DOCUMENTS 5,488,065 1/1996 Roth ....................................... 514/504

*Primary Examiner*—Melvyn I. Marquis
*Attorney, Agent, or Firm*—Peter J. Georges; Louis A. Morris

[57] ABSTRACT

This invention relates to antimicrobial compositions comprising a phenoxyarsine as the active antimicrobial substance and a solvent, which is a compound of the formula

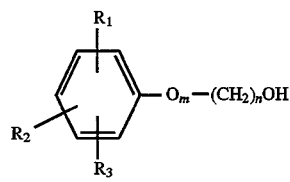

wherein $R_1$, $R_2$ and $R_3$ are hydrogen or lower alkyl, m is 0 or 1 and n is 1 or 2. The compositions are suitable for the antimicrobial finishing of synthetic materials.

10 Claims, No Drawings

ANTIMICROBIAL COMPOSITIONS

This application is a continuation of application Ser. No. 06/859,189, filed Apr. 28, 1986, now U.S. Pat. No. 5,488,065, granted Jan. 30, 1996, in turn a continuation of Ser. No. 06/670,246, filed Nov. 13, 1984 (abandoned).

SUMMARY OF THE INVENTION

This invention is directed to antimicrobial compositions comprising a phenoxyarsine compound as the active antimicrobial ingredient and a solvent which is a compound of the formula

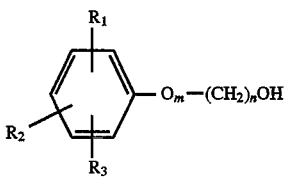

wherein $R_1$, $R_2$ and $R_3$ are hydrogen or lower alkyl, m is 0 or 1 and n is 1 or 2. This invention is also directed to the use of the antimicrobial compositions in protecting synthetic materials against microbial attack.

BACKGROUND OF THE INVENTION

It is known that synthetic materials can be protected against microbial influences by incorporating antimicrobially active substances in these materials. In particular, it is known to incorporate phenoxyarsines, for example 10,10'-oxybis-phenoxyarsine, as an antimicrobial agent to protect these synthetic materials. This is generally carried out by treating the plasticizer used in the manufacture of these synthetic materials, for example in the manufacture of vinyl resins such as polyvinyl chloride, with a solution of the phenoxyarsine. Various solvents for the phenoxyarsine have been proposed for this purpose. For example, phenols and aliphatic alcohols such as nonylphenol, as well as certain phosphites and phosphonates such as tris (dipropyleneglycyl)phosphite are disclosed in U.S. Pat. No. 3,288,674. In various respects these solvents have disadvantages which are to some extent considerable, namely:

—low dissolving capacity at room temperature,
—high viscosity and difficulties associated therewith during the processing,
—troublesome odors,
—low boiling points,
—unsatisfactory miscibility with the plasticizers usually used in the plastics industry, and
—unfavorable toxicological properties.

It has been found that it is possible to overcome the above-noted disadvantages by using certain organic solvents in combination with phenoxyarsine antimicrobial agents.

DETAILED DESCRIPTION OF THE INVENTION

The invention is directed to antimicrobial compositions comprising a phenoxyarsine compound as the antimicrobial ingredient and a solvent having the formula

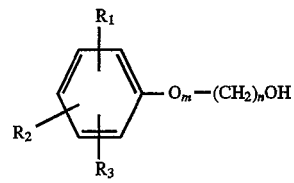

wherein $R_1$, $R_2$ and $R_3$ are hydrogen or lower alkyl ($C_1$–$C_7$), m is 0 or 1 and n is 1 or 2.

The antimicrobial compositions of this invention are useful for the antimicrobial finishing of synthetic materials, for example synthetic plastic materials.

As used herein, the term "antimicrobial" also encompasses fungistatic or fungicidal activity.

Compounds of formula I which are useful in the present invention include benzyl alcohol, 2-phenylethanol and 2-phenoxyethanol. The preferred solvent of formula I is benzyl alcohol.

Further examples of compounds of formula I are those in which $R_1$, $R_2$ and $R_3$ are each a butyl group, i.e. tributyl-substituted compounds of formula I.

Phenoxyarsines that are useful in the present invention include all phenoxyarsines which are conventionally used for the antimicrobial finishing of synthetic materials. Examples of such phenoxyarsine compounds are those described in U.S. Pat. No. 3,689,449 and No. 4,049,822. The preferred phenoxyarsine compound is 10,10'-oxybis-phenoxyarsine.

The antimicrobial compositions of the present invention comprise about 10% to about 50% by weight of the antimicrobial phenoxyarsine compound and from about 50% to about 90% of the solvent of formula I. The preferred amount of phenoxyarsine is from about 20 to about 30% by weight, and the preferred phenoxyarsine compound is 10,10'-oxybisphenoxyarsine.

A further aspect of the present invention is directed to compositions which, besides the phenoxyarsine and the solvent, additionally contain at least one plasticizer. The phenoxyarsine and the plasticizer are usually incorporated in the synthetic material by means of such a composition. Such a composition is obtained, for example, by mixing a 20% stock solution (20% solution of the phenoxyarsine in a solvent of formula with a plasticizer. The resulting product contains about 1–2% by weight of phenoxyarsine based on the total amount of plasticizer, solvent and phenoxyarsine. These compositions are used in the synthetic products of manufacturing industries for the antimicrobial finishing of films, floor coverings, wall coverings, shower curtains, bath mats, door handles, stair handrails, pipe bandages, etc. These compositions can be incorporated readily in the particular synthetic product using conventional machines, whereby, for example, in the production of polyvinyl chloride the usual processing temperatures of up to about 180° C. are also compatible.

Plasticizers which can be employed in the present invention include the following:
- esters of polybasic acids (such as phthalic acid, adipic acid, trimellitic acid, sebacic acid) with monovalent alcohols, such as ethylhexyl alcohol, isodecyl alcohol, isotridecyl alcohol, having molecular weights of about 250 to about 500;
- polyesters of glycols, such as 1,2-propylene glycol, neopentyl glycol, with dibasic acids, such as adipic acid, sebacic acid, having molecular weights of about 600 to about 1200;
- epoxidated vegetable oils, such as soya epoxide, castor oil epoxide;

phosphoric acid esters, such as tricresyl phosphate, tri-2-ethylhexyl phosphate.

Synthetic materials which can be protected by the compositions of the present invention include vinyl resins, namely homopolymers of vinyl chloride, manufactured by emulsion, suspension or mass polymerization, and copolymers of vinyl chloride with vinyl acetate, maleic acid, vinylidene chloride, acrylonitrile etc., manufactured by emulsion or suspension polymerization, as well as by grafting polymerization.

Polyvinyl chloride is the preferred synthetic material.

A further aspect of the present invention is therefore concerned with a synthetic material, especially a polyvinyl chloride material, which has been manufactured using one of the mixtures referred to above.

The present invention is also concerned with a method for the manufacture of an antimicrobial mixture or of a mixture suitable for the antimicrobial finishing of synthetic materials, which method comprises dissolving a phenoxyarsine, especially. 10,10'-oxybisphenoxyarsine, in a solvent of formula I above and, if desired, incorporating this solution in a plasticizer.

Further, the present invention is concerned with a process for the manufacture of a synthetic material, especially a polyvinyl chloride material, which process comprises dissolving a phenoxyarsine, especially 10,10'-oxybisphenoxyarsine, in a solvent of formula I above, incorporating the solution obtained in a plasticizer and using the plasticizer mixture obtained in the manufacture of synthetic materials. These plasticizer mixtures can also contain antioxidants such as, for example, sterically hindered phenols [such as 2,6-ditert. butyl-p-cresol; amine compounds such as, for example, N,N'-dicyclohexyl-p-phenyienediamine; sulfur(II) compounds such as, for example, dilauryl thiodipropionate]. The synthetic materials manufactured using these plasticizer mixtures can also contain lubricants. Examples of lubricants which can be utilized are metal soaps, e.g. calcium stearate, zinc stearate, or waxes, e.g. carnauba wax. These plasticizer mixtures can be incorporated in polyvinyl chloride mixtures in an amount of up to about 1.5% (in the case of a phenoxyarsine content of 2%) or 3% (in the case of a phenoxyarsine content of 1%), based on the vinyl system.

The following Examples illustrate the invention.

EXAMPLE 1

Various concentrates of 10,10'-oxybisphenoxyarsine (OBPA) with various solvents are compiled in Table 1, whereby in each case the minimum temperature required for the dissolution of the OBPA is reported (RT=room temperature).

TABLE 1

| Components | Concentrate [wt. %] | | |
|---|---|---|---|
| | A | B | C |
| OBPA | 20 | 20 | 20 |
| Benzyl alcohol | 80 | | |
| 2-Phenylethanol | | 80 | |
| 2-Phenoxyethanol | | | 80 |
| Dissolution temperature [°C.] | RT | 50 | 150 |

The above concentrates A, B and C are frost-resistant and can be stored in suitable containers for an almost unlimited period.

EXAMPLE 2

The concentrates A, B and C set forth in Table 1 are mixed at room temperature with various plasticizers, to commercial products containing 1 or 2 wt. % of OBPA. The resulting mixtures are compiled in Table 2.

TABLE 2

| Components | Products [wt. %] | | | | | | | | | | | |
|---|---|---|---|---|---|---|---|---|---|---|---|---|
| | A | B | C | D | E | F | G | H | J | K | L | M |
| Concentrate | | | | | | | | | | | | |
| A | 5 | | | 10 | | | 5 | | | 10 | | |
| B | | 5 | | | 10 | | | 5 | | | 10 | |
| C | | | 5 | | | 10 | | | 5 | | | 10 |
| Diisodecyl-phthalate | 95 | 95 | 95 | 90 | 90 | 90 | | | | | | |
| Soya oil, epoxidated | | | | | | | 95 | 95 | 95 | 90 | 90 | 90 |
| OBPA content | 1 | 1 | 1 | 2 | 2 | 2 | 1 | 1 | 1 | 2 | 2 | 2 |

These products are also frost-resistant and can be stored in suitable containers for an almost unlimited period.

EXAMPLE 3

The products A–M of Table 2 can be used in polyvinyl chloride mixtures, especially in an amount 1.5% (in the case of an OBPA content of 2%) or 3% (in the case of an OBPA content of 1%) based on the vinyl system.

The vinyl system can have the following composition, for example:

| | Wt. % |
|---|---|
| Suspension PVC (K = 70–72) | 57.55 |
| Plasticizer mixture in accordance with this invention (2% OBPA) | 1.50 |
| Other plasticizer (butylphenylphosphate) | 27.90 |
| Antioxidant (2,6-di-tert.butyl-cresol) | 0.05 |
| Burgess clay | 8.60 |
| Dibasic lead phthalate | 3.50 |
| Dibasic lead stearate | 0.60 |
| Lubricant (calcium stearate) | 0.30 |
| | 100.0 |

Under "plasticizer mixture" there is to be understood herein one of the products A–M of Example 2. In this manner there is obtained a vinyl mixture containing 0.03% or 300 ppm of OBPA, which is sufficient for an antimicrobial protection effect.

I claim:

1. An antimicrobial composition which is suitable for the antimicrobial finishing of synthetic materials, comprising a phenoxyarsine as the antimicrobial agent and a solvent, wherein said solvent is a compound of the formula

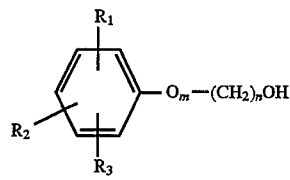

I wherein $R_1$, $R_2$ and $R_3$ are hydrogen or lower alkyl, m is 0 or 1 and n is 1 2.

2. A composition comprising a plasticizer suitable for use as a polymer processing aid and, in an amount at least sufficient to impart microbiocidal properties to the composition, a microbiocidal compound which is present in the composition as the solute in an aryl alkanol solvent, said microbiocidal compound being a phenoxarsine.

3. A composition comprising a plasticizer suitable for use as a polymer processing aid and, in an amount at least sufficient to impart microbiocidal properties to the composition, a microbiocidal compound which is present in the composition as the solute in a solvent of the following formula:

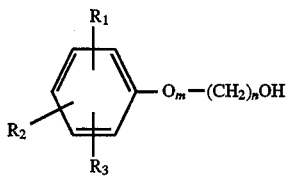

I wherein $R_1$, $R_2$ and $R_3$ are hydrogen or lower alkyl, m is 0 or 1 and n is 1 or 2, said microbiocidal compound being a phenoxarsine.

4. The composition of claim 3, wherein the solvent is benzyl alcohol.

5. The composition of claim 3, wherein the solvent is 2-phenylethanol.

6. A composition of claim 3, wherein the solvent is 2-phenoxyethanol.

7. A composition according to claim 3, wherein the phenoxarsine is 10,10'-oxybisphenoxarsine.

8. A composition according to claim 4, wherein the phenoxarsine is 10,10'-oxybisphenoxarsine.

9. A composition according to claim 5, wherein the phenoxarsine is 10,10'-oxybisphenoxarsine.

10. A composition according to claim 6, wherein the phenoxarsine is 10,10'-oxybisphenoxarsine.

\* \* \* \* \*